United States Patent [19]
Wilson

[11] Patent Number: 4,730,949
[45] Date of Patent: Mar. 15, 1988

[54] SURGICAL SCRUB BRUSH

[75] Inventor: Earl D. Wilson, Ingleside, Ill.

[73] Assignee: The Kendall Company, Boston, Mass.

[21] Appl. No.: 843,446

[22] Filed: Mar. 24, 1986

[51] Int. Cl.$^4$ .......................... A46B 11/02; A47K 7/03
[52] U.S. Cl. ...................................... 401/132; 401/24; 401/37; 401/196; 604/3
[58] Field of Search ................... 401/132, 196, 28, 37, 401/24; 604/3

[56] References Cited

U.S. PATENT DOCUMENTS

| 3,485,562 | 12/1969 | Hidden et al. | 401/196 X |
| 3,704,072 | 11/1972 | Kaufman | 401/28 X |
| 3,966,335 | 6/1976 | Abramson | 401/196 |
| 3,998,559 | 12/1976 | Hoyt | 401/132 |
| 4,148,318 | 4/1979 | Meyer | 401/132 X |
| 4,469,463 | 9/1984 | Van Overloop | 401/134 |
| 4,479,277 | 10/1984 | Gilman et al. | 15/111 |

FOREIGN PATENT DOCUMENTS 2125280  3/1984  United Kingdom ................ 401/132

Primary Examiner—Steven A. Bratlie
Attorney, Agent, or Firm—Donald N. Halgren

[57] ABSTRACT

The present invention comprises a scrub brush for medical cleaning purposes having a housing including a base with a plurality of walls comprising a reservoir for containment of treatment material. A foil type sealing material is disposed across the walls to seal the treatment material in the reservoir. A foam element is arranged on the housing, and a piercing means is arranged to break the foil and soak the foam.

3 Claims, 4 Drawing Figures

U.S. Patent  Mar. 15, 1988  4,730,949
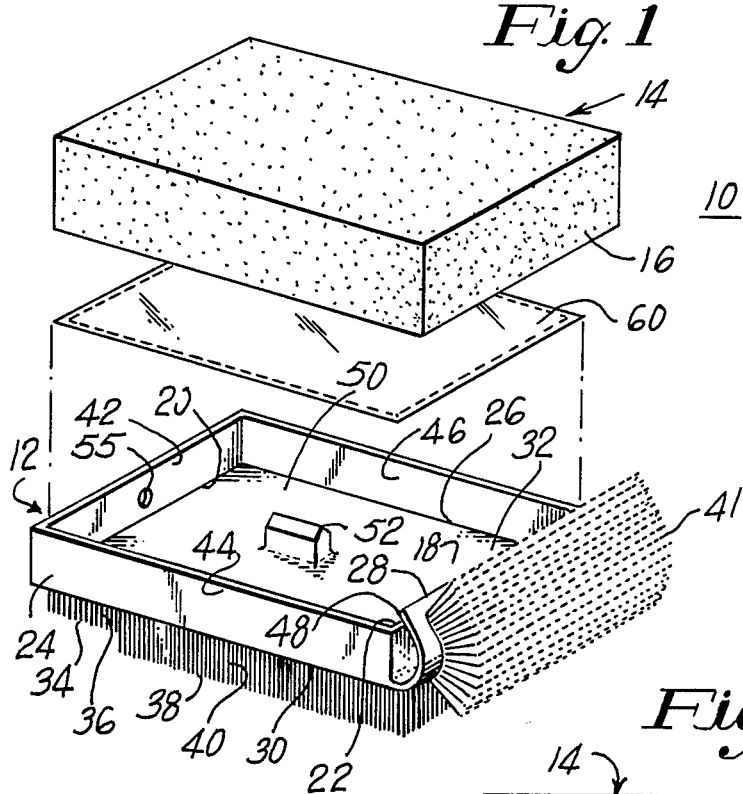
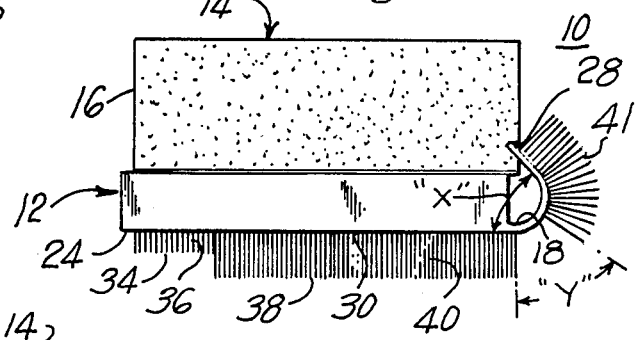
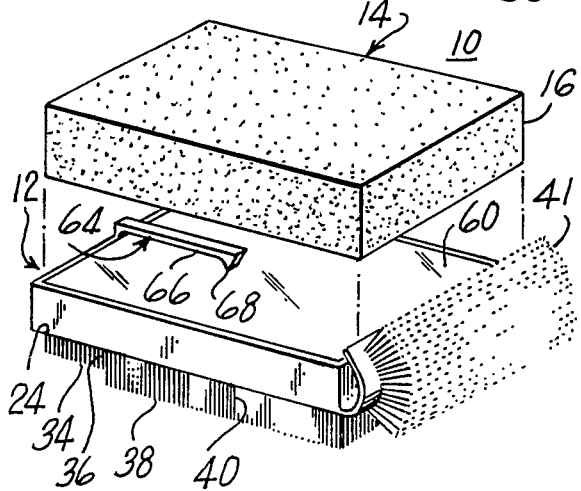
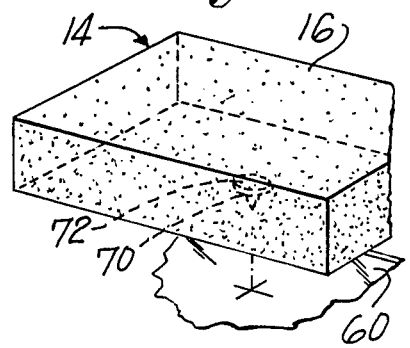

SURGICAL SCRUB BRUSH

BACKGROUND OF THE INVENTION

(1) Field of the Invention

This invention relates to brushes generally and in particular to surgical scrub brushes containing their own cleansing agents.

2. PRIOR ART

Preparation for surgical procedures, such as a surgical operation, require that the operating room personnel be antiseptically cleansed and that the patient as well be antiseptically cleansed in the area to be operated upon. Surgical cleansing apparatus having containment devices for applying a cleansing fluid onto a surface may be seen in U.S. Pat. No. 1,615,581 comprising a chamber having a frangible cap closing its neck, and a needle supported in an inlet which permits the cap to be punctured to discharge the liquid therein on demand. Liquid would feed into a brush to be applied to the skin surfaces of the doctor/nurse/patient using the device.

A further invention is shown in U.S. Pat. No. 3,135,007 wherein a pad is disposed over a sealing disk on a chamber. A piercing element is disposed within the pad to pierce the sealing member. A surgical scrubbing device is shown in U.S. Pat. No. 3,467,978 wherein a body contains a brush on one side thereof and a sponge on the other side thereof with a pointed finger element for cleaning hard to reach or difficult areas which need cleaning. A further surgical scrubbing device is shown in U.S. Pat. No. 4,181,446 wherein a brush back has bristles on one face, which face is bendable to swing the bristles into opposed relation for scrubbing an internal or concave surface. A further cleansing device is shown in U.S. Pat. No. 3,998,559 wherein a pair of reservoirs are attached to a sponge which must be flexed with both hands to pierce a membrane therebetween. The sponge itself is bent to permit the cleansing to take place. Further scrub sponges are shown in U.S. Pat. Nos. 4,330,220 and 4,469,463 wherein a reservoir is enclosed in a sponge. A sponge also encloses a piercable element which is arranged to rupture a reservoir to permit the outflow of cleansing material therefrom.

A sponge and brush combination is shown in U.S. Pat. No. 4,420,853 or in a housing as disposed on arrangement of bristles on one side thereof and a soft foam material on the other side of the housing thereof. An antimicrobial solution may be placed on the foam block of the '853 Patent.

It is an object of the present invention to provide a scrub device which contains its own reservoir of antimicrobial or cleansing compounds.

It is another object of the present invention to provide a combination brush sponge which is activatable utilizing only one hand.

It is further object of the present invention wherein the brush thereof has means therewithin to facilitate cleansing of difficult to reach areas such as fingernails or the like.

It is a further object of the present invention to provide a housing which is not yieldable to fracture its reservoir contained therewithin, permitting structural integrity to remain therewith.

BRIEF SUMMARY OF THE INVENTION

The present invention comprises a surgical scrub brush having a foam element on one side thereof. The brush is made integral with a housing, preferably of rectangular shape. The housing acts as a reservoir for cleansing or antibacterial compounds therewithin. On the outside of one side of the housing there are a plurality of bristles disposed thereon. On one end of the housing there may be an arcuate array of bristles of generally the same type and construction as disposed on the large surface of the housing. An arcuate gap is disposed between the bristles on the large flat surface of housing and those on the end of the housing in the arcuate array thereof. Disposed above the housing and the material therewithin, is the foam sponge attached to the periphery of the uppermost edge of the housing.

One embodiment of the present invention comprises a piercing means disposed therein and preferably integral with the inside bottom surface of the housing. The piercing means extends near the planar surface of the distal rim of the walls of the housing. A piercable film is disposed on those peripheral portions of the housing walls if the material to be contained in the housing, is of a liquid nature. The sponge then would be disposed contiguous to the piercable film adjacent the peripheral edge of the housing walls. A further embodiment includes a piercing element which is secured to the inwardly directed side of the sponge element, so as to effectuate piercing of the film from the outside thereof.

If the cleansing agent to be contained within the housing reservoir is of a non-liquid nature, e.g. a powder, then the film would not necessarily be utilized between the housing and the foam therebetween.

With a liquid agent within the housing reservoir, the user of the scrub device would merely press down slightly on the foam material inwardly so as to cause the piercing means to puncture the film. Thus the fluid therewithin would spread to the foam on an as needed basis. The gap between the planar bristle arrangement and the arcuate bristle arrangement permits and facilitates cleansing of areas which are otherwise difficult to reach with a standard brush or cleaning element.

BRIEF DESCRIPTION OF THE DRAWINGS

The objects and advantages of the present invention will become more apparent when viewed in conjunction with the following drawings in which:

FIG. 1 is an exploded, perspective view illustrating a scrub brush of the present invention;

FIG. 2 is a side elevational view of the brush showing the gap disposed between the bristle arrangement;

FIG. 3 is an exploded view in perspective illustrating an alternative embodiment of the invention; and FIG. 4 is a view of an alternative embodiment of the film piercing means.

DESCRIPTION OF THE PREFERRED EMBODIMENTS

Referring now to the drawings in detail and particularly to FIG. 1, there is shown a self-contained scrub brush 10 having a housing 12 comprised of any suitable plastic material such as polyethylene, and a handle member 14 comprising a generally rectangular block 16 of suitable foam material, such as polyurethane foam.

The housing 12 is preferably of a rectangular shape, having a rectangular base 18, a backside 20, a front side 22 and a pair of opposed sides 24 and 26 extending between the backside 20 and the front side 22. The housing 12 has a forward portion 28 extending outwardly from the base 18 on the front side 22 which may be curved backwardly upon itself at an acute angle "x", such as between 60° and 70° relative to the base 18 as shown in FIG. 2. The base 18 has a lower surface 30, and an opposed upper surface 32. As shown, the base 18 has a lateral area 34 of relatively short bristles 36, such as 7 mm. in length extending from the lower surface 30 adjacent the backside 20. Also the base 18 has a region 38 over substantially the remainder of base 18 of relatively long bristles 40, such as 12 mm. in length extending from the lower surface 30 of the base 18. The forward portion 28 has relatively long bristles "40" such as 12 mm. in length, extending outwardly from the forward portion 28, with the bristles 41 on the forward portion 28 preferably having a length approximately equal the length of the bristles 40 in the region 38 of the base 18. An arcuate segment "Y" of the forward portion 28 is void of bristles whatsoever as shown in FIG. 2. The arcuate segment "Y" is approximately 30°.

The housing 12 has an upstanding back wall 42 adjacent the backside 20 and upstanding sidewall 44 adjacent the side 24 and an upstanding wall 46 adjacent the other side 26, and an upstanding front wall 48 adjacent the forward portion 28. The back wall 42 and the sidewalls 44 and 46 and the front wall 48 define a reservoir or cavity 50.

A puncture means 52 may be molded into the housing 12, in a manner as shown in FIG. 1. The piercing means 52 may comprise a relatively sharp or pointed straight edge member extending upwardly from the upper surface 32 of the base 18, to a height of approximately the wall periphery. A supply means or loading orifice 55 is shown disposed through, for example, the back wall 42. The orifice 55 may be used for injecting a fluid or powdered cleansing agent into the housing, to provide the cleaning or treatment fluid or substance therein.

A thin film of foil 60 or the like, shown in FIG. 1 is attachable at its periphery to the upper edge of the walls of the housing 12. The film 60 may be heat sealed or adhered thereto by an appropriate adhesive. The block 16 of sponge-like foam material may also be adhered to the film 60 by an adhesive or the like around the periphery.

An alternative embodiment is shown in FIG. 3, wherein a film piercing means 64 is shown disposed over the film 60. The film piercing means 64 may comprise an arm 66 with a point 68 at its distal end. The point 68 is directed towards the film 60 for puncture thereof. The proximal end of the piercing means 64 may be attached to one of the walls of the housing 12.

A further embodiment of the piercing means is shown in FIG. 4, where a sharp pointed element 70, having base means 72 is secured to the sponge-like block 14, to also permit the piercing of the film 60 from outside. That is, piercing the film 60 from a location between the sponge-like block 14 on the outer side of the film 60.

In construction of the scrub brush 10, the preferred manner of assembly would be to injection mold the housing 12 including the bristles and the preferred piercing means 52 in one operation. The film 60 would then be secured to the periphery of the walls 42, 44, 46 and 48. The block 16 of foam material would then be adhered to the outer side of the film 60. A quantity of cleansing agent would then be injected through the orifice 55 in the wall 42 of the housing 12 so as to provide cleaning material in the reservoir 50. The orifice 55 would be sealed in a known manner such as by heating the plastic sealing the same.

In use, the scrub brush 10 may merely be pressed inwardly by a user, on its foam block 16 so as to effectuate piercing of the film 60 by the piercing means 52 within the housing 12 or by the piercing means 64 or 70 outwardly of the film 60. The cleansing or antibacterial treatment material, preferably a fluid within the housing would then be caused to be spread into the foam block 16 to effectuate its use. The other manner of filling the housing 12 with a fluid for cleaning or antibacterial purposes would be to fill the housing prior to the attachment of the film 60 about the periphery of the walls 42, 44, 46 and 48.

The arcuate gap in the bristle configuration at the forward end thereof, permits the scrub brush 10 user to get at hard to reach places such as in the corners between fingers, or under fingernails or the like.

Although the invention has been described in some detail, it is intended that the appended claims be interpreted as exemplary only.

I claim:

1. A single use scrub brush for medical cleansing purposes, comprising:
   a housing having a base having an arrangement of walls disposed about said base;
   a plurality of bristles extending from said base;
   an array of bristles disposed outwardly adjacent one edge of said base;
   a foam element secured to the housing;
   a resevoir within said housing for containment of treating material;
   a sealing means comprising a sheet of foil material arranged between said resevoir and said foam element about the periphery of said walls of said housing; and
   a sharp piercing means comprising an arm fixedly arranged between said sealing means and said foam element from the wall of said housing, to pierce said sealing means upon selected pressure applied to said foam element.

2. A scrub brush for medical cleansing purposes as recited in claim 1, wherein a supply means is disposed through said housing to permit the filling of said resevoir therein with said treatment material.

3. A scrub brush for medical cleansing purposes as recited in claim 1, wherein said array of bristles are disposed away from said bristles on said base of said housing, by an arc of 25° to 40°, to permit the bristles adjacent thereto to reach hard to scrub locations.

* * * * *